United States Patent [19]

Korteweg

[11] Patent Number: 4,553,966
[45] Date of Patent: Nov. 19, 1985

[54] DEVICE FOR DRAINING BODY FLUIDS AND IRRIGATING SOLUTIONS

[75] Inventor: Wayne Korteweg, Ledyard, Conn.

[73] Assignee: Americal Corporation, Mystic, Conn.

[21] Appl. No.: 533,222

[22] Filed: Sep. 19, 1983

[51] Int. Cl.⁴ .............................................. A61M 1/00
[52] U.S. Cl. .................................. 604/317; 128/760; 222/187; 239/44
[58] Field of Search ............... 604/128, 317, 352, 362, 604/374, 327, 328, 330, 246, 358, 8–10; 222/187; 239/44, 49, 50; 128/760, 762

[56] References Cited

U.S. PATENT DOCUMENTS

| | | | |
|---|---|---|---|
| 2,457,851 | 1/1949 | Taft | 222/187 |
| 4,246,901 | 1/1981 | Frosch et al. | 604/329 |
| 4,344,432 | 8/1982 | Pankav | 604/327 |

*Primary Examiner*—Stephen C. Pellegrino
*Attorney, Agent, or Firm*—Ostrolenk, Faber, Gerb & Soffen

[57] ABSTRACT

A device for draining body fluids and irrigating solutions adapted for utilization with respect to operations on the human body, such as brain operations, eye operations, micro surgery and other types of operations, wherein a wick material, which may be used as a single unit or wherein a wick material, which may be separated or cut into sections, is connected to a drainage funnel or pouch which may be secured by adhesive or otherwise at the site of the operation and wherein the wick material is capable of capillary absorption of fluids initially and when saturated, of acting in a siphon-like manner to draw fluids into the pouch. The pouch itself at its lower end is connected by a tube to a collection bag which is appropriately vented. For smaller incisions or for utilization at sites where fluid is to be drawn from relatively small areas or openings, the wick material instead of comprising a number of sections cut and shaped from the original wick material may comprise a single slender wick member which may readily be located at the said site. In forming the wick material for utilization with respect to absorption of fluids from a larger incision, at least one of the sections which is formed may extend only to the edge of the incision in order to draw fluid which might otherwise be absorbed by the drape around the incision, thereby ensuring that all of the fluid is withdrawn into a pouch in which, if necessary, it may be examined or tested prior to being disposed of.

9 Claims, 5 Drawing Figures

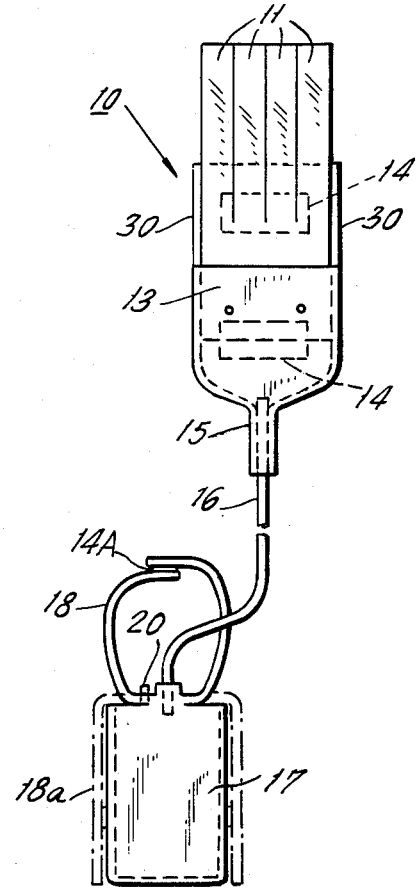
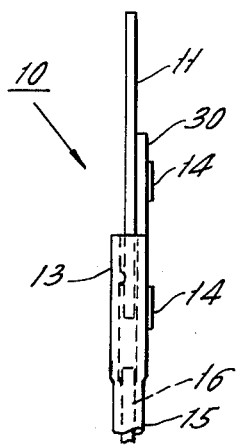
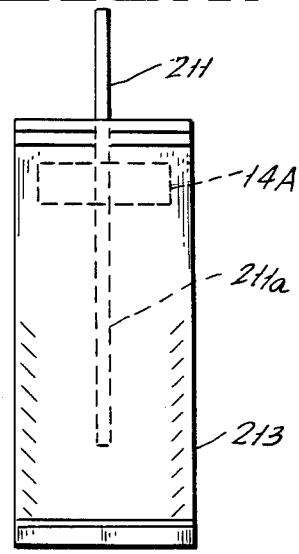
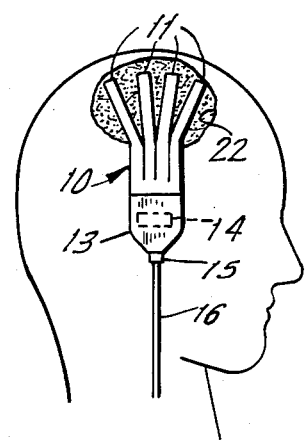
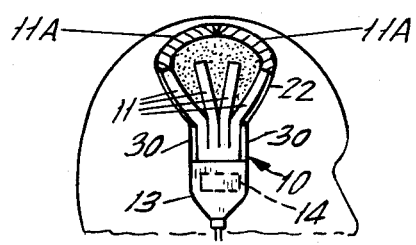

DEVICE FOR DRAINING BODY FLUIDS AND IRRIGATING SOLUTIONS

BACKGROUND OF THE INVENTION

The present invention relates to a device for removing fluid from an operation or drainage site.

In order to accomplish the result and effect proper drainage, the present invention utilizes a series of devices among which are a wicking material, such as cotton, gauze, fibrous substances, foam, sponges and other types of connective material which may be used which cause a wicking action. Essentially, the wicking action which is primarily capillary in its operation in the initial stages results, after the material has become substantially saturated, in a gravity flow and siphoning action which will permit the fluid that is generated during an operation to flow into an appropriate receptacle, preferably a funnel-shaped device that contains a drain or method of catching the fluid from the wicking portion and directing it into a tube or conduit, enabling the drainage solution to leave the site in a collected manner. Preferably, the fluid thus drained is directed to a storage container, pouch or bag where the entire solution is retained until the procedure is complete and a determination is made that no further need exists to examine the drained fluid so that it may be disposed of.

In order to accomplish the desired results, the material of choice is a hydroxylated polyvinyl acetal sponge having the registered trademark "MEROCEL®" which is a sponge material accepted by the FDA and that contains a radio-opaque material. The latter is provided to facilitate detection of the sponge by X-ray. A material should be used that allows entry without fear of fragmenting. The preferred material is known to have an excellent ability to absorb by capillary action drawing the liquid to a point at a level with the source, then because of gravity, releasing the flow in a siphon-type manner. The system is therefore self-priming.

BRIEF SUMMARY OF THE INVENTION

The primary object of the present invention, therefore is the provision of a draining apparatus particularly for draining fluid from the site such as an operation, by the utilization of a wicking material, a siphoning action results in transmitting the fluid to a receptacle, pocket or funnel-shaped device that contains the drain and constitutes a method of catching the fluid from the wicking portion and directing it into a tube or other means enabling the drained solution to exit the surgical site into a collection system.

A further object is the arrangement of the wicking material into a plurality of bands, segments or fingers which may be spread over a wide area to be drained.

The foregoing and many other objects of the present invention will become apparent from the following description and the accompanying drawings.

BRIEF DESCRIPTION OF THE DRAWINGS

FIG. 1 is an elevation of the novel draining device of the present invention including the wicking material, the pocket or funnel-shaped device for receiving the drained material and the tube which drains the solution into a storage container, pouch or bag for examination, if needed, and disposal.

FIG. 2 is a schematic view showing the positioning of the drainage device of FIG. 1 at a craniotomy incision.

FIG. 3 is a side view of a portion of the drainage device of FIG. 1.

FIG. 4 is an elevation of a modified form of the invention for utilization in another type of operation such as for eye drainage, wherein the wicking material is connected directly to a collecting, examining or disposal pouch.

FIG. 5 is a schematic fragmentary view of a modification of the present invention wherein an additional wicking member extends to the edge of the incision opening.

DESCRIPTION OF THE PREFERRED EMBODIMENT

Referring to FIGS. 1, 2 and 3, the drainage device of the present invention comprises a wicking section 10, having a plurality of spreadable elements 11, which are connected as shown particularly in FIG. 3 into the interior of a collector or pouch 13, constituting a drainage funnel and having appropriate means secured thereto including, for instance, a tape 14 for adhesion. The lower end of the pouch 13 is provided with a collar 15 which is connected by a tube 16 to the collection bag 17 which is provided with appropriate means 18 for supporting the bag in any suitable manner and is also provided with a vent 20 to prevent back pressure from interfering with the flow from the funnel-shaped drainage pouch 13 into the collection bag 17.

As shown particularly in FIG. 2, the element 10 is supported in any suitable manner at the site of the incision 22 of the operation, the wick elements 11 being spread appropriately across the site to provide rapid absorption by capillary action initally of the fluids generated in the site 22 of the operation during the operation. These fluids, although initially collected by capillary action in the wicking element 10, when the wick element 10 becomes saturated, are moved by a siphoning action past the edge of the incision 22 and flow regularly into the drainage funnel 13 from which they flow through tube 16 into the collection pouch 17.

As seen in FIG. 1, the pouch 17 may be provided with straps 18 which may be secured by double stick or double surface adhesive 14a, to form a handle, which facilitates fastening and securement. The handles 18 may initially be fabricated at 18a adjacent the pouch 17 and moved to the handle position. They may be formed of or have secured thereto double stick adhesive to faciliiate manipulation, positioning or securement.

The essential element here is the combination of the wicking action and siphoning action in that the initial absorption into the members 11 of the wick 10 is capillary but as the member 10 becomes fully saturated, the system becomes a siphoning action which ensures that all the fluid which may enter the members 11 of the wick 10 will be collected and siphoned off into the drainage funnel 13 and thereafter into the collection pouch 17. Since the members 11 of the wick 10 are highly flexible, they may be easily spread over the site of the incision and readily moved aside as the operation takes place and readily moved to other areas of the incision where necessary in order to ensure complete absorption.

As seen in FIGS. 1, 3 and 5, a flap 30 may be provided at the top of the funnel 13 which may be placed over the drape up to the wound site to limit contact of the wicking section 10 with areas, other than the wicking system, that may absorb fluid.

The material of the wick member 10 and its arms 11 is preferably a hydroxylated polyvinyl acetal sponge having the trade name "MEROCEL®", which is an FDA accepted sponge that contains radio-opaque material, making it visible to X-ray to ensure that all elements of the sponge have been removed when the operation is completed. The essential point is that the material must have an excellent ability to absorb by drawing of liquids to a point at least level with the source and then because of gravity and siphoning action releasing a flow into the drainage funnel 13 by siphoning action and thereafter continuously through the tube 16 into the pouch 17.

In FIG. 5 there is shown additional wicking members which modify the present invention in which one of the arms 11 of the wicking member 10 is placed on the additional wicking members 11A to extend and obtain a greater wicking area which may include the entire perimeter of the incision 22. This additional member 11A may be of the same material as 11. 11A then becomes an extension of 11 following the same pattern of flow through 10 into the drainage funnel 13 through tube 16 into the collection pouch 17.

In another modified form of the present invenion, as shown in FIG. 4, a form of the device is shown for utilization in other types of operations or in other types of procedures, such as for eye drainage where in this case a small version 211 of the wick material is arranged so that it may be laid into a small incision or may be laid into an area where fluid is to be withdrawn (not necessarily from an incision). The fluid may thereafter be drawn by capillary action into the wick 211 and then through the extension 211a which is in the pouch 213 where it may be collected.

Thus, the essential elements of the present invention comprise first the utilization of a wicking material that is constructed with a drainage pouch in a single unit with a wick attached. A collection device is also provided to provide a holding bag or pouch for the entire amount of fluid which is delivered. The fluid is drained from the area by utilization of capillary action and then collected in a holding bag or pouch.

The wicking material 10-11, 11A or 211 or 211a may be provided in a form other than that which is eventually to be used and may be cut into a desired set of fingers or elements of appropriate length for the particular application and to permit it to be spread out. The immediate flowthrough of the fluid through the tube 16 into the collection pouch 17 draws off the blood and debris and does not permit the clogging of the blood or the clotting of debris to hamper drainage.

The collection device as herein described may be attached in any suitable manner as by adhesive tape or other means to any part of the body where fluid is to be collected. The collection device is disposable as a whole. The system comprises an open system that collects by initial capillary attraction and then by siphon action into a closed pouch system or into any other suitable receptacle.

In the foregoing, the present invention has been described solely in connection with preferred illustrative embodiments thereof. Since many variations and modifications of the present invention will now be obvious to those skilled in the art, it is preferred that the scope of this invention be determined not by the specific disclosures herein contained, but only by the appended claims.

What is claimed is:

1. A fluid collection and disposal system for utilization in connection with the drawing off of fluids during medical procedures or operations comprising a wicking material having a high capillary absorption capacity capable of being saturated to become a siphoning material when a portion thereof passes the edge of an area from which fluid is to be drawn; and means connected to said wicking material to receive said fluid; the wick material being separated into a plurality of sections or fingers which may be spread over the site of the procedure which is being performed.

2. The fluid collection and disposal system of claim 1, wherein additional wicking members touching said fingers may be placed in or on a site to be drained, said additional members acting as extension of the wick.

3. The fluid collection and disposal system of claim 1, wherein said wick material comprises a relatively narrow section capable of being placed in a relatively small area of the body.

4. The fluid collection and disposal system of claim 1, wherein the device is particularly adapted for utilization for brain operations and the wick material is cut and spread to cover various portions of the opening through the skull to the brain in order to collect and drain fluid.

5. The fluid collection and disposal system of claim 1, wherein the wicking material is a hydroxylated polyvinyl acetal sponge containing a radio-opaque material.

6. The fluid collection and disposal system of claim 1, wherein the device comprises wick material having a relatively narrow section capable of collecting eye drainage fluid directly into a pouch and adapted for utilization in eye operations.

7. The fluid collection and disposal system of claim 2, wherein the wicking material is connected to a drainage device into which fluid from the wick material may drain.

8. The fluid collection and disposal system of claim 7, wherein the drainage system comprises a drainage funnel with a tube at its lower end for removal of the fluid.

9. The fluid collection and disposal system of claim 1, wherein the wick material is capable of being cut into a plurality of sections which may be spread over the area.

* * * * *